(12) United States Patent
Danhof

(10) Patent No.: US 10,213,425 B2
(45) Date of Patent: Feb. 26, 2019

(54) ROLE OF N-2-HYDROXY-ETHYL-PIPERAZINE-N'-2-ETHANE SULFONIC ACID (HEPES) IN PAIN CONTROL AND REVERSAL OF DEMYELINIZATION INJURY

(71) Applicant: Bespoke Bioscience, LLC, Dallas, TX (US)

(72) Inventor: Ivan E. Danhof, Grand Prairie, TX (US)

(73) Assignee: BESPOKE BIOSCIENCE, LLC, Dallas, TX (US)

( * ) Notice: Subject to any disclaimer, the term of this patent is extended or adjusted under 35 U.S.C. 154(b) by 0 days.

(21) Appl. No.: 15/725,007

(22) Filed: Oct. 4, 2017

(65) Prior Publication Data

US 2018/0028530 A1 Feb. 1, 2018

Related U.S. Application Data

(63) Continuation of application No. 14/481,582, filed on Sep. 9, 2014, now Pat. No. 9,867,820, which is a continuation of application No. 12/885,404, filed on Sep. 17, 2010, now Pat. No. 8,883,855.

(60) Provisional application No. 61/243,464, filed on Sep. 17, 2009.

(51) Int. Cl.
A61K 31/495 (2006.01)

(52) U.S. Cl.
CPC .................. A61K 31/495 (2013.01)

(58) Field of Classification Search
CPC .................................. A61K 31/495
See application file for complete search history.

(56) References Cited

U.S. PATENT DOCUMENTS

| | | | |
|---|---|---|---|
| 5,248,680 A | 9/1993 | Bloomfield | |
| 5,643,562 A | 7/1997 | Kisilevsky et al. | |
| 5,716,959 A * | 2/1998 | Theodore | A61K 31/185 424/531 |
| 5,728,375 A | 3/1998 | Kisilvesky et al. | |
| 6,071,919 A * | 6/2000 | Theodore | A61K 31/185 424/531 |
| 8,883,855 B2 | 11/2014 | Danhof | |
| 2009/0149464 A1 | 6/2009 | Sergeant et al. | |
| 2014/0378467 A1 | 12/2014 | Danhof | |

FOREIGN PATENT DOCUMENTS

| | | | |
|---|---|---|---|
| AR | 78290 A1 | 10/2011 | |
| AU | 2014206220 A1 | 8/2014 | |
| AU | 2010295445 B2 | 1/2015 | |
| CA | 2774375 A1 | 3/2011 | |
| CN | 102612366 A | 7/2012 | |
| CN | 103977405 A | 8/2014 | |
| EP | 2011491 A1 | 7/2009 | |
| EP | 2163246 A1 | 3/2010 | |
| EP | 2477626 A2 | 1/2013 | |
| EP | 2835133 A1 | 2/2015 | |
| HK | 1199621 A1 | 7/2015 | |
| IN | 2499DEN2012 A | 8/2015 | |
| JP | 2013505264 A | 2/2013 | |
| JP | 201552006 A | 3/2015 | |
| JP | 2015129150 A | 7/2015 | |
| KR | 20120081151 A | 7/2012 | |
| MX | 331477 | 7/2015 | |
| NZ | 598861 | 9/2010 | |
| SG | 179191 A1 | 4/2012 | |
| TW | 201127813 A | 6/2011 | |
| TW | 201440769 A | 11/2014 | |
| WO | 97029745 | 8/1997 | |
| WO | WO-9729745 A1 * | 8/1997 | ........... A61K 31/185 |
| WO | 2009004082 A2 | 1/2009 | |
| WO | 2011035212 A2 | 3/2011 | |

OTHER PUBLICATIONS

Theodore et al., Preliminary Evaluation of a Fixed Dose of Zwitterionic Piperazine (TVZ-7) in Clinical Cancer, Cancer Biotherapy & Radiopharmaceuticals, vol. 12 (5), 1997, 351-353.*

Theodore et al., Pilot Ascending Dose Tolerance Study of Parenterally Administered 4-(2 Hydroxyethyl)-l-piperazine Ethane Sulfonic Acid (TVZ-7) in Dogs, Cancer Biotherapy and Radiopharmaceuticals 12(5):345-349, Oct. 1997.*

Bhagwager, et al., "Increased Brain GABA Concentrations Following Acute Administration of a Selective Serotonin Reuptake Inhibitor," Am. J. Psychiatry (2004), 161:368-370.

Bhupinder, et al., "Improvement of impaired memory in mice by taurine," Database Biosis, Biosciences Information Services, Neural Plasticity, vol. 7:4, 2000, pp. 245-249.

Chuang, et al., "Delayed Neuropathy and Myelopathy after Organophosphate Intoxication," N. Engl. J. Med., vol. 347, No. 14, Oct. 3, 2002.

European Patent Office, Extended European Search Report for EP 10 81 7952.4 dated Mar. 20, 2013.

European Patent Office, Extended European Search Report for EP 14 191 925.8 dated Jan. 12, 2015.

Fountoulakis, et al., "Treatment Guidelines for Bipolar Disorder: A Critical Review," Journal of Affective Disorders 86 (2005) pp. 1-10.

International Search Report and Written Opinion dated May 24, 2001 in connection with International Application No. PCT/US2010/049405.

Kokoz, et al., "Selective Cytostatic and Neurotoxic Effects of Avermectins and Activation of the GABAα Receptors," Bioscience Reports, vol. 19, No. 6, 1999.

(Continued)

*Primary Examiner* — Svetlana M Ivanova

(74) *Attorney, Agent, or Firm* — Edwin S. Flores; Chalker Flores, LLP

(57) ABSTRACT

Compositions and therapeutic uses of HEPES and derivatives in the treatment of pain associated with cancers and side-effects including post-chemotherapy cognitive impairment are disclosed herein. HEPES is also used to treat neurodegenerative and neurological diseases, demyelinization injuries, and side-effects and withdrawal symptoms associated with benzodiazepines, anti-depressants, and other neurological agents.

4 Claims, No Drawings

(56) References Cited

OTHER PUBLICATIONS

Letter from Applied Biomedical Institutional Review Board to Dr. Ivan E. Danhof regarding approval of study for "Safety and Dose Determination Study of TVZ 7 in Subjects with Pain Associated with Solid Tumor Cancer Including Cases with Bone Metastases," dated Nov. 6, 1996, 1 pg.
Letter of Protest of T. Ronald Theodore dated Jan. 5, 2015, 38 pages.
Li, et al., "Voltage-dependent transient currents of human and rat 5-HT transporters (SERT) are blocked by HEPES and ion channel ligands," FEBS Letters, Elsevier, Amsterdam, NL, Feb. 27, 2002, vol. 513:2-3, pp. 247-252.
Malaysia Substantive Examination Adverse Report and Search Report, Application No. PI 2012001195 dated Aug. 14, 2015, 3 pp.
Memorandum and Letter from Bob McConachie to Ron Theodore and Dr. Robert J. Temple of the Office of Drug Evaluation, FDA, regarding Initial Submission for Physician's IND Safety and Dose Determination Study of TVZ-7 in Subject with Pain Associated with Solid Tumor Cancer Including Cases with Bone Metastases, dated Nov. 7, 1996, 3 pages.
Parent, et al., "Intraseptal Infusions of Muscimol Impair Spontaneous Alternation Performance: Infusions of Glucose into the Hippocampus, but Not the Medial Septum, Reverse the Deficit," Neurobiology of Learning and Memory, vol. 68, 1997, pp. 75-85.
Petegnief, V, "Taurine Analog Modulation of Taurine Uptake by Two Different Mechanisms in Cultured Glial Cells," Biochemical Pharmacology, vol. 49, No. 3, pp. 399-410.
Stapleton, et al., "Effects of In-vivo Administration of Taurine and HEPES on the Inflammatory Response in Rats," J. Pharm. Pharacol., vol. 46, Feb. 4, 1994, pp. 745-750.
Theodore, et al, "Pilot ascending Dose Tolerance Study of Parenterally Administered 4-(2-hydroxyethyl) Piperazine Ethane Sulfonic Acid," Cancer Biotherapy & Radiopharmaceuticals, vol. 12, No. 5, 1997, pp. 345-349.
Theodore, T. Ronald, et al., "Preliminary Evaluation of a Fixed Dose of Zwitterionic Piperazine (TVZ-7) in Clinical Cancer," Cancer Biotherapy & Radiopharmaceuticals, vol. 12, No. 5, 1997, pp. 351-353.
Tunnicluff, et al., "Competitive inhibition of gamma-aminobutyric acid receptor binding by N-2-hydroxyethylpiperazine-N'-2-e-ethanesulfonic acid and related buffers," Journal of Neurochemistry, Mar. 1, 1981, Vo. 36:3, pp. 1122-1126.
Vohra, Bhupinder, P.S., et al, "Improvement of impaired memory in mice by Taurine," Neural Plasticity, vol. 7, No. 4, 2000, pp. 245-259.
Zeng, et al., "Role of bicarbonate ion in mediating decreased synaptic conductance in benzodiazepine tolerant hippocampal CA 1 pyramidal neurons" Brain Research 868, Mar. 1, 2000, pp. 202-214.
Zhu, et al., "Protection by a Taurine Supplemented Diet from Lead-Induced Deficits of Long-Term Potentiation/Depotentiation in Dentate Gyrus of Rats In Vivo," Neuroscience, vol. 134, Mar. 11, 2005, pp. 215-224.

* cited by examiner

ROLE OF N-2-HYDROXY-ETHYL-PIPERAZINE-N'-2-ETHANE SULFONIC ACID (HEPES) IN PAIN CONTROL AND REVERSAL OF DEMYELINIZATION INJURY

CROSS-REFERENCE TO RELATED APPLICATIONS

This patent application is a continuation patent application of U.S. patent application Ser. No. 14/481,582 filed on Sep. 9, 2014 and entitled "Role of N-2-Hydroxy-Ethyl-Piperazine-N'-2-Ethane Sulfonic Acid (HEPES) in Pain Control and Reversal of Demyelinization Injury," which is a continuation patent application of U.S. patent application Ser. No. 12/885,404 filed on Sep. 17, 2010 and entitled "Role of N-2-Hydroxy-Ethyl-Piperazine-N'-2-Ethane Sulfonic Acid (HEPES) in Pain Control and Reversal of Demyelinization Injury," now U.S. Pat. No. 8,883,855 issued on Nov. 11, 2014, which claims priority to U.S. Provisional Application Ser. No. 61/243,464 filed Sep. 17, 2009, the entire contents of which are incorporated herein by reference.

STATEMENT OF FEDERALLY FUNDED RESEARCH

None.

INCORPORATION-BY-REFERENCE OF MATERIALS FILED ON COMPACT DISC

None.

TECHNICAL FIELD OF THE INVENTION

The present invention relates in general to the field of pain control post-chemotherapy, and more particularly, to compositions and use of N-2-hydroxy-ethyl-piperazine-N'-2-ethane sulfonic acid (HEPES) as pain control agents and to reverse demyelinization injury.

BACKGROUND OF THE INVENTION

Without limiting the scope of the invention, its background is described in connection with compositions and therapeutic uses of piperazine based compounds and their derivatives.

U.S. Pat. No. 5,248,680 issued to Bloomfield (1993) describes zwitterionic compounds selected from, taurine (2-aminoethanesulphonic acid), 2(N-morpholino)ethanesulphonic acid (MES), N-(2-acetamido)iminodiacetic acid (ADA), piperazine-N,N'bis(2-ethanesulphonic acid (PIPES), N-(2-acetamido)-2-aminoethanesulphonic acid (ACES), N,N-bis(2-hydroxyethyl)-2-aminoethanesulfonic acid (BES), 3-(N-morpholino)propanesulphonic acid (MOPS), N—N[tris(hydroxymethyl)-methyl]-2-aminoethanesulphonic acid (TES), N-2-hydroxyethylpiperazine-N'-2-ethanesulphonic acid (HEPES), N-2-hydroxyethylpiperazine-N'3-propanesulphonic acid (H)EPPS), 2-(cyclohexylamino) ethanesulphonic acid (CHES) or 3-(cyclohexylamino) propanesulphonic acid (CAPS), and their N-halo derivatives that can be used separately or in combination in the treatment of related clinical conditions by stimulating myeloperoxidase activity, which in turn stimulates hypochlorous acid production in vivo, which leads inter alia to enhanced leukotriene inactivation.

U.S. Pat. No. 5,716,959 issued to Theodore and Van Zandt (1998) discloses a substituted piperazine zwitterion composition containing, for example, as an active ingredient, HEPES (N-2 Hydroxyethylpiperazine-N'-2 Ethane Sulfonic Acid), and method useful for treatment of cancer, autoimmune, arthritis and other mammalian diseases.

U.S. Patent Application No. 20090149464 (Sergeant et al., 2009) describes the use of 1,4-bis(3-aminoalkyl)piperazine derivatives for the manufacture of a pharmaceutical composition intended for the treatment of neurodegenerative diseases, related neurodegenerative diseases, developmental diseases or cancer. The instant invention is also directed to some specific 1,4-bis(3-aminoalkyl)piperazine derivatives and pharmaceutical composition including them.

SUMMARY OF THE INVENTION

The present invention describes the use of HEPES and derivatives thereof as an analgesic agent, an antitumor agent, for the stabilization of cellular, especially neuronal membranes, and for the reversal of demyelinization injury. Separate embodiments of the present invention detail the use of HEPES in treating neurodegenerative, demyelination, neurological diseases, and also for treating neuropsychiatric disorders like Tourette's syndrome. Compositions of HEPES as described herein are also used to treat withdrawal symptoms, side-effects or both following treatment with anti-depressants and selective serotonin inhibitors (SSRI). HEPES is also used as an analgesic agent to treat pain associated with one or more cancers and for side-effects post-chemotherapy including post-chemotherapy cognitive impairment.

In one embodiment the present invention discloses a pharmaceutical composition for treating withdrawal symptoms, side-effects or both following treatment with anti-depressants, selective serotonin inhibitors (SSRI), or other neurological agents in a subject comprising, N-2-hydroxy-ethyl-piperazine-N'-2-ethane sulfonic acid (HEPES) and derivatives thereof dissolved in sterile water, buffer, saline or other pharmaceutically acceptable carriers in an amount sufficient to treat withdrawal symptoms, side-effects or both following treatment with one or more anti-depressants, one or more selective serotonin inhibitors (S SRI), or other neurological agents. The composition of the present invention may optionally contain one or more excipients, diluents, extended or controlled release agents, coloring agents, preservatives or any combinations thereof. In one aspect the HEPES is dissolved in sterile water for injection for oral, subcutaneous, parenteral, intravenous, peritoneal, or intramuscular administration and is administered once daily on a body weight basis at 10-100 mg/kg. In another aspect the anti-depressants are selected from the group consisting of benzodiazepines, SSRIs, Serotonin-norepinephrine reuptake inhibitors (SNRIs), Noradrenergic and specific serotonergic antidepressants (NaSSAs), Norepinephrine (noradrenaline) reuptake inhibitors (NRIs), Norepinephrine-dopamine reuptake inhibitors (NDRIs), Selective serotonin reuptake enhancers (SSREs), Melatonergic agonists, Tricyclic anti-depressants (TCAs), and Monoamine oxidase inhibitor (MAOIs) and the SSRIs comprise citalopram, escitalopram, fluoxetine, fluvoxamine, paroxetine, sertraline, zimelidine or any combinations thereof.

In a related embodiment the present invention describes a method of treating withdrawal symptoms, side-effects or both following treatment with anti-depressants, selective serotonin inhibitors (SSRI), or other neurological agents in a subject in a human subject comprising the steps of:

identifying a subject in need for treatment against the withdrawal symptoms, side-effects or both following treatment with anti-depressants, selective serotonin inhibitors (SSRI), or other neurological agents and administering a pharmaceutical composition comprising N-2-hydroxy-ethyl-piperazine-N'-2-ethane sulfonic acid (HEPES) and derivatives thereof dissolved in sterile water, buffer, saline or other pharmaceutically acceptable carriers once daily at a dosage of 10-100 mg/kg of body weight, wherein the pharmaceutical composition is administered orally, subcutaneously, parenterally, intravenously, peritoneally, or intramuscularly. In one aspect the anti-depressant comprises benzodiazepines or derivatives thereof.

In another embodiment the present invention described a pharmaceutical composition for treating one or more neurodegenerative diseases, treating one or more demyelination diseases or both in a subject comprising, N-2-hydroxy-ethyl-piperazine-N'-2-ethane sulfonic acid (HEPES) and derivatives thereof dissolved in sterile water, buffer, saline or other pharmaceutically acceptable carriers in an amount sufficient to treat the one or more neurodegenerative diseases, the one or more demyelination diseases or both and one or more optional excipients, diluents, extended or controlled release agents, coloring agents, preservatives or any combinations thereof. In one aspect the one or more demyelination diseases comprise multiple sclerosis, transverse myelitis, Devic's disease, progressive multifocal leukoencephalopathy, optic neuritis, Leukodystrophies, Guillain-Barré syndrome, Charcot-Marie-Tooth Disease or any combinations thereof. In another aspect the one or more neurodegenerative diseases comprise Parkinson's disease, Alper's disease, Alzheimer's disease, Lou Gehrig's Disease Corticobasal degeneration, Creutzfeldt-Jakob disease, Frontotemporal lobar degeneration Huntington's disease, Krabbe's disease, Multiple System Atrophy, Multiple sclerosis, Pick's disease, Primary lateral sclerosis, Progressive Supranuclear Palsy, Refsum's disease, Sandhoff disease, Schilder's disease, Spinal muscular atrophy, Steele-Richardson-Olszewski disease or any combinations thereof. In specific aspects the demyelinating disease is Multiple Sclerosis and the neurodegenerative disease is Parkinson's disease. In yet another aspect the HEPES is dissolved in sterile water for injection for oral, subcutaneous, parenteral, intravenous, peritoneal, or intramuscular administration and the composition is administered once daily on a body weight basis at 10-100 mg/kg and treats the one or more demyelination diseases by restoring, repairing, and/or regenerating a myelin sheath.

In yet another embodiment the present invention describes a method of treating one or more neurodegenerative diseases, treating one or more demyelination diseases or both in a human subject comprising the steps of: (i) identifying a subject in need for treatment against the one or more neurodegenerative diseases, treating one or more demyelination diseases or both and (ii) administering a pharmaceutical composition comprising N-2-hydroxy-ethyl-piperazine-N'-2-ethane sulfonic acid (HEPES) and derivatives thereof dissolved in sterile water, buffer, saline or other pharmaceutically acceptable carriers once daily at a dosage of 10-100 mg/kg of body weight, wherein the pharmaceutical composition is administered orally, subcutaneously, parenterally, intravenously, peritoneally, or intramuscularly. In specific aspects of the method of the present invention the demyelinating disease is Multiple Sclerosis and the neurodegenerative disease is Parkinson's disease and the composition treats the one or more demyelination diseases by restoring, repairing, and/or regenerating a myelin sheath.

Another embodiment of the present invention relates to a pharmaceutical composition for treating symptoms associated with one or more neurological diseases, one or more neuropsychiatric disorders or both in a subject comprising, N-2-hydroxy-ethyl-piperazine-N'-2-ethane sulfonic acid (HEPES) and derivatives thereof dissolved in sterile water, buffer, saline or other pharmaceutically acceptable carriers in an amount sufficient to treat the one or more neurodegenerative diseases, the one or more demyelination diseases or both. The composition as described in the present invention may optionally contain one or more excipients, diluents, extended or controlled release agents, coloring agents, preservatives or any combinations thereof. In one aspect the one or more neurological or neuropsychiatric disorders comprise cerebral palsy, Tourette's syndrome, choreia, athetosis, bipolar disorder, schizophrenia or any combinations thereof. In another aspect the HEPES is dissolved in sterile water for injection for oral, subcutaneous, parenteral, intravenous, peritoneal, or intramuscular administration. In yet another aspect the composition is administered once daily on a body weight basis at 10-100 mg/kg.

In one embodiment the present invention details a method for treating symptoms associated one or more neurological diseases, one or more neuropsychiatric disorders or both in a human subject comprising the steps of: identifying a subject in need for treatment against the symptoms associated with the one or more neurological diseases, the one or more neuropsychiatric disorders or both and administering a pharmaceutical composition comprising N-2-hydroxy-ethyl-piperazine-N'-2-ethane sulfonic acid (HEPES) and derivatives thereof dissolved in sterile water, buffer, saline or other pharmaceutically acceptable carriers once daily at a dosage of 10-100 mg/kg of body weight, wherein the pharmaceutical composition is administered orally, subcutaneously, parenterally, intravenously, peritoneally, or intramuscularly. In one aspect of the method of the present invention the neurological disease is cerebral palsy, choreia, or athetosis and the neuropsychiatric disorder is Tourette's syndrome.

One embodiment of the present invention discloses a pharmaceutical composition for treating pain associated with a cancer, side-effects following cancer treatment including post-chemotherapy cognitive impairment or both in a subject comprising: N-2-hydroxy-ethyl-piperazine-N'-2-ethane sulfonic acid (HEPES) and derivatives thereof dissolved in sterile water, buffer, saline or other pharmaceutically acceptable carriers in an amount sufficient to treat the pain associated with the cancer, side-effects following the cancer treatment including post-chemotherapy cognitive impairment or both and one or more optional excipients, diluents, extended or controlled release agents, coloring agents, preservatives or any combinations thereof. In one aspect the composition is used to treat pain associated with pancreatic cancer, breast cancer, colorectal cancer, ovarian cancer, lung cancer, cervical cancer, gastric cancer, liver cancer, melanomas, brain tumors, multiple myeloma, prostate cancer, and bladder cancer. In another aspect the composition is used to treat post-chemotherapy cognitive impairment following a breast cancer treatment. In yet another aspect the HEPES is dissolved in sterile water for injection for oral, subcutaneous, parenteral, intravenous, peritoneal, or intramuscular administration and is administered once daily on a body weight basis at 10-100 mg/kg.

In a related embodiment the present invention discloses a method of treating pain associated with a cancer, side-effects following cancer treatment including post-chemotherapy cognitive impairment or both in a human subject comprising the steps of: (i) identifying a subject in need for treatment against the pain associated with the cancer, side-effects following cancer treatment including post-chemotherapy cognitive impairment or both and (ii) administering a pharmaceutical composition comprising N-2-hydroxy-ethyl-piperazine-N'-2-ethane sulfonic acid (HEPES) and derivatives thereof dissolved in sterile water, buffer, saline or other pharmaceutically acceptable carriers once daily at a dosage of 10-100 mg/kg of body weight, wherein the pharmaceutical composition is administered orally, subcutaneously, parenterally, intravenously, peritoneally, or intramuscularly. In specific aspects the composition is used to pain associated with a pancreatic cancer and to treat post-chemotherapy cognitive impairment following a breast cancer treatment.

In one embodiment the present invention describes a pharmaceutical composition for treating pancreatic cancer in a subject comprising: N-2-hydroxy-ethyl-piperazine-N'-2-ethane sulfonic acid (HEPES) and derivatives thereof dissolved in sterile water, buffer, saline or other pharmaceutically acceptable carriers in an amount sufficient to treat the pancreatic cancer and one or more optional excipients, diluents, extended or controlled release agents, coloring agents, preservatives or any combinations thereof.

In another embodiment the present invention is a method of treating pancreatic cancer in a human subject comprising the steps of: identifying a subject in need for treatment against the pancreatic cancer and administering a pharmaceutical composition comprising N-2-hydroxy-ethyl-piperazine-N'-2-ethane sulfonic acid (HEPES) and derivatives thereof dissolved in sterile water, buffer, saline or other pharmaceutically acceptable carriers once daily at a dosage of 10-100 mg/kg of body weight, wherein the pharmaceutical composition is administered orally, subcutaneously, parenterally, intravenously, peritoneally, or intramuscularly.

BRIEF DESCRIPTION OF THE DRAWINGS

None.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "HEPES" as used in various embodiments of the present invention refers to N-2-hydroxyethylpiperazine-N'-2-ethanesulfonic acid ($C_8H_{18}N_2O_4S$).

The term "withdrawal symptoms" as used herein is intended to include those symptoms known to those skilled in the art attendant upon forced discontinuation of ingestion of a narcotic substance or a drug, and includes vomiting, severe muscle spasms, agitation, lacramation from the nose and eyes, uncontrollable urination, nausea, and, in severe cases, convulsions, respiratory failure, and cardiac arrest.

The term "neurodegenerative disease" (or "neurological disease") as used herein refers to a disease or disorder of the nervous system, particularly involving the brain, that manifests with symptoms characteristic of brain or nerve dysfunction, e.g., short-term or long-term memory lapse or defects, dementia, cognition defects, balance and coordination problems, and emotional and behavioral deficiencies.

The term "demyelinating disease" refers to any pathological process that results in the degradation or loss of the myelin sheath surrounding an axon including, but not limited to, Multiple Sclerosis and Guillain-Barre syndrome. As used herein, the term "Multiple Sclerosis" refers to a demyelinating disorder of the central nervous system characterized, anatomically, by sclerotic plaques in the brain and spinal cord producing symptoms including (but not limited to) visual loss, diplopia, nystagmus, dysarthria, weakness, paresthesias, and bladder abnormalities.

As used herein, the term "neuropsychiatric disorder" refers to a disease having a pathophysiological component of attenuated NMDA receptor-mediated neurotransmission. Examples of such disorders include schizophrenia, Alzheimer's disease, autism, depression, benign forgetfulness, childhood learning disorders, closed head injury, and attention deficit disorder.

The term "cancer" as used herein refers to a cellular disorder characterized by uncontrolled or disregulated cell proliferation, decreased cellular differentiation, inappropriate ability to invade surrounding tissue, and/or ability to establish new growth at ectopic sites. The term also includes, but is not limited to, solid tumors and blood borne tumors. The term "cancer" encompasses diseases of skin, tissues, organs, bone, cartilage, blood, and vessels and includes primary and metastatic cancers. The term "chemotherapy" as used herein is defined as the treatment of disease with chemical substances. Used herein chemotherapy refers to application of anti-neoplastic chemicals to an individual with cancer. The goal of chemotherapy is selective toxicity to cancer cells.

As used herein the terms "administration of" or "administering a" compound refers to providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" indicates that the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

The term "excipients", as used herein, is intended to include one or more compatible solid or liquid filler diluents or encapsulating substances which are suitable for administration to a human subject. Some examples of substances which can serve as excipients include sugars such as lactose, glucose and sucrose; starches such as corn-starch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; and alginic acid; as well as other non-toxic compatible substances used in pharmaceutical formulations. Wetting agents and lubricants such as sodium lauryl sulfate, as well as coloring agents, flavoring agents, sweetening agents (including non-nutritive sweeteners such as aspartame and saccharin), tableting agents, stabilizers, antioxidants, cooling agents, and preservatives, can also be present.

By "pharmaceutically acceptable" it is to be understood that the carrier, diluent or excipient must be compatible with the other ingredients of the formulation and not be deleterious to the recipient thereof.

The present invention uses a N-2-Hydroxy-ethyl-piperazine-N'-2-ethane sulfonic acid commercially known as "HEPES" is a zwitterionic molecule commonly and widely used as a buffer in cell cultures of both animal and human origin. Studies have demonstrated that HEPES has the least cytotoxicity of all the known buffers. HEPES is a piperazine-based zwitterionic molecule. Piperazine compounds are derived from the phenothiazines. Phenothiazines have been approved by the FDA as anti-anxiety and anti-psychotic agents. Non-zwitterionic piperazine compounds have been approved by the FDA as antihelminthic agents. Other piperazine-based molecules are approved as food additives. Mechanisms of action of HEPES include the following:

(i) Analgesic activity, possibly related to prolonged antianandamide action, without the significant side-effects in contrast to the opiates;

(ii) Anti-tumor activity possibly related to mechanisms previously found with promethazine;

(iii) Stabilization of cellular, especially neuronal membranes, possibly by regulation of various ion channels; and (iv) Reversal of demyelination injury.

The product, HEPES, is produced in ultra-pure form and is available from GIBCOL Technologies, Inc. The product is administered on a body weight basis with the determined minimal effective daily dosage of 70-75 mg/kg. The material may be safely given either by oral or parenteral routes. The present inventors have on a number of occasions observed that, the medication can be taken by both routes without any significant side-effects. The administered product is prepared by a compounding pharmacist, with the dosage of each patient recipient being individualized.

Clinical Cases of Various Neurological Disorders

Demyelinating Diseases:

Myelin sheaths, which cover many nerve fibers, are composed of lipoprotein layers formed in early life. Myelin formed by the oligodendroglia in the CNS differ chemically and immunologically from that formed by the Schwann cells peripherally, but both types serve the same function of promoting transmission of a neural impulse along the axon.

1. Multiple Sclerosis: Many congenital metabolic disorders may result in defective myelin sheath formation. Demyelination in later life is a feature of many neurological disorders, which may arise from a plethora of causes, e.g., damage from local injury, ischemia, toxic agents, or metabolic disorders. Extensive myelin loss is often followed by axonal degeneration and often by cell body degeneration, both of which may be irreversible.

Fortunately, spontaneous remyelination may occur in many instances, and repair, regeneration, and complete recovery may occur with rapid restoration of neural functions in some cases, while in others, there is unrelenting progression and worsening neural injury, with complete loss of physiological functioning. Central demyelination (i.e., of the spinal cord, brain, or optic nerves) is the predominant finding in the primary demyelinating diseases, for which there is no known etiology. The most well-known condition is Multiple Sclerosis (MS). The exacerbations and remissions of symptoms of MS serve as the prime example of injury and recovery. Symptoms of MS are extremely varied and diverse and may be considered in several categories: (i) Mental—apathy, poor judgment, depression, emotional lability, (ii) Cranial Nerve Dysfunction—$3^{rd}$, $4^{th}$, and $6^{th}$ cranial nerve problems often associated with mild nystagmus with fatigue, (iii) Sensory Neural Function—diminished position sense, multiple paresthesias especially involving the extremities, lateral trunk, and sides of the face, (iv) Motor Neural Function—diminished superficial reflexes, increased, often significantly, deep tendon reflexes and Babinskis, intention tremor, and generalized muscular weakness, (iv) Autonomic Neural Function—urinary urgency and hesitation, often slight incontinence, constipation.

Example 1

B.F. is a 42-year old public elementary school teacher, who was diagnosed with MS when she was 35. She has had significant recurring symptomatology every 4-6 months with different symptom profiles, suggestive of variable sites of involvement.

Mentally, she often experienced periods of lack of concentration and follow-through of immediate projects, generalized muscular stiffness and lack of fine motor coordination with episodes of lurching gait and imbalance. Very bothersome was her manual discoordination which adversely influenced her writing on the chalk board. Indeed, the symptoms were so frequent that her teaching contract was not renewed. She subsequently obtained employment at an academically excellent small Episcopal school where the classes were small and the stress level was considerably less compared with the public school system.

Despite these changes of venue, she had more frequent exacerbations and remissions and experienced multiple medication programs with her very concerned neurologist physician. She continued to use block letters on the blackboard rather than cursive black-board writing as a form of communicating with her students.

After a particularly severe episode of problems, she completely lost the ability to write (e.g., writing a payment check) owing to the loss of manual sensory function and erratic motor movements. The present inventors were asked to see her by the school administrator, who served as her friend and confidant. She was started on HEPES at a dosage of 5,000 mg (5 tsp) daily—2 tsp with breakfast, 1 tsp mid-afternoon, and 2 tsp at bedtime. After only three days of treatment she regained the ability to write cursively and sign her name in a legible fashion. She has been continued on the oral medication and has maintained her motor function as well as being free of new exacerbations.

2. Cerebral Palsy: The term cerebral palsy (CP) identifies children with non-progressive spasticity, ataxia, or involuntary movements. Between 0.1-0.2% of children have CP symptoms, while up to 1% of premature newborns or those small for gestational age are affected. The causes have been difficult to uncover but prematurity, in-utero disorders, neonatal jaundice and perinatal asphyxia are thought to play a role with birth trauma and perinatal asphyxia or kernicterus of special interest. CP syndromes are grouped into four main categories, spastic, athetoid, ataxia, and mixed forms. Spastic paraplegia is especially common after premature birth, spastic quadriplegia after perinatal sepsis, and athetoid and dystonic forms after perinatal asphyxia or kernicterus. Spastic cases occur in about 70% of cases. The spasticity is due to upper motor neurone involvement with mild to severe affections of motor functioning, e.g., hemiplegia, paraplegia, quadriplegia, or diplegia. It may take up to two years to make a definitive diagnosis of CP type. Treatments include physical therapy, occupational therapy, bracing, orthopedic surgery, and speech training. As with all chronically handicapped children, parents need assistance and guidance in understanding the child's status and potential and in relieving their own feelings.

Example 2

M.S. is a 17-year old boy of Chinese extraction, whose birthing was extremely difficult, and very probably associated with some degree of neonatal asphyxia, although this was not seriously reflected in the Apgar Score. M.S. has had superb medical care all his life long with loving and supportive parents able to provide recommended therapies.

Despite the abundance of treatment programs, it required nearly five years for M.S. to walk slowly in an unassisted manner. Amazingly, his speech pattern and intellectual capabilities were remarkably functional. A major problem was his significant dysfunction with motor skills in his hands. M.S. was given an oral dosage of HEPES of 5,000 mg daily (2 tsps with breakfast, 1 tsp mid-afternoon, and 2 tsps at bedtime). After three weeks his walking pattern showed considerable improvement with significant reduction in ataxic characteristics, the movement and control of his hands and especially his fingers improved to the point where he could selectively (upon oral command) depress the correct key on the computer. After 8 months of therapy, his walking and manual skills have improved to 85% of normal. He became devoted to spending several hours daily on the computer and the amount of knowledge he has acquired and retained is, indeed, phenomenal. The change in this young man has been outstanding and truly gratifying to his parents, his siblings, and especially his physicians.

3. Post Chemotherapy Cognitive Impairment (PCCI): Post chemotherapy cognitive impairment (also known as chemotherapy-induced cognitive dysfunction, chemo brain or chemo brain fog describes the cognitive impairment, which can result from chemotherapy treatment. Approximately 30-40% of persons who undergo chemotherapy experience some level of PCCI. The phenomenon initially came to light because of the large number of breast cancer survivors who complained of memory, fluency, and other cognitive liabilities that impeded their ability to function as they had prior to chemotherapy. In most cases there is no known way of reducing the effects of chemotherapeutic agents related to taxanes, thalidomide and platinum-based compounds, but cognizance needs to be taken of the innate ability of the nerves to repair themselves, at least to some extent, to metabolize and excrete these compounds, to change the permeability of the blood-brain barrier, reverse the damage to DNA including the shortening of telomeres and cellular oxidative stress. Other theories suggest vascular injury, inflammation, autoimmunity, anemia and the presence of epsilon-4-version of the apolipoprotein-E gene. The compared systems most affected by chemotherapy drugs include visual and semantic memory, attention and motor coordination. These effects can impair the patient's ability to intelligently understand and make decisions regarding treatment, performance in school or employment, and reduce significantly the quality of life.

Cognitive dysfunction (or brain fog) is usually associated with poor mental function, especially regarding concepts, words, memories, and is characterized by confusion, forgetfulness, difficulty in concentration, and maintenance of focus. Sleep patterns are often disturbed and defective REM (dream) sleep may result in serious depressive disorders. One nurse's experience: "One of the first things that makes us realize that there is something wrong with us is the inability to perform intellectually like we once did. We seemingly accept the increasing pain, muscle spasms, the insomnia, but when we keep forgetting our own phone number, red flags go up. We lose things—misplace others—on a route we know, we get lost—we forget where we're going—shopping lists lose their importance because we keep forgetting to bring them—we lose our car in parking lots time and time again—we come home from shopping and realize we bought the exact same things the day before. We forget friends' names. We stop in mid-conversation because we've forgotten what we were talking about. We start using gadgets and date books in order to keep track of our normal to-do list. If we handle our own checkbook, we gradually have more and more trouble with it. Even taking a shower is a major effort because we don't remember whether we've rinsed the shampoo out of our hair—we lose the washcloth—we drop everything—we forget whether we rinsed all those hard-to-reach areas. What were once functions we handled without thought, we now need to consciously review every aspect of the process before it occurs. We laugh about it. We learn to "cover" the errors with laughter. But we're embarrassed and silently questioning our own sanity. We worry about brain tumors and Alzheimer's because we know the problem is far more extensive than other people are seeing. As one colleague said, "I can no longer rely on me!" So we joke about it with each other. This is not everyday forgetfulness that everyone experiences from time to time. This is a 24-hour, seven days-a-week continual struggle to appear and act normally. It's been proven by SPECT and PET scans of the brain. It really IS all in our heads—and it's real." The multiplicity of "treatments" for brain fog indicates the deficit of information which resides with the medical professionals. Suggested therapies include: antioxidants, cognitive behavior modification, erythropoietin injections, stimulant drugs, hypnosis, thyroid replacement therapy, neurofeedback treatments.

Example 3

KL is a 45-year old woman who, prior to her diagnosis of breast cancer, has been in charge of the family business involving a host of necessary transactions, including maintenance of financial records and tax liabilities.

Post chemotherapy she had profound difficulty remembering what day it was, what time it was, had she taken her morning bath, what to cook for any meal, forgetfulness as to daily chores, transporting her children to school-sponsored events, suddenly breaking telephone conversations with her concerned mother without any recall of the action.

The major deficit business-wise was the inability to perform simple mathematical calculations. These shortcomings resulted in tax consequences of which she was totally unaware. Chronic, unrelenting physical fatigue was creating a serious impediment in the family constellation especially with her husband, who did not realize what was happening. He thought she "was going bonkers!"

Her mother inquired as to what could be done to alleviate the rapidly deteriorating family problems. A trial on HEPES was recommended as the symptoms were, at least in part, related to demyelination. She was started on oral HEPES, 5,000 mg daily in divided doses. Within three days she indicated that the "cloud" had "risen." It was still there, but her cognitive abilities, especially as to current events and her obligations in achieving her goals, were improved. Within a few more days, the cloud was ascending higher, and after a month the "cloud" was gone. She continues to show improvement in a gratifying manner.

Parkinson's Disease: Parkinson's Disease is the $4^{th}$ most common neurodegenerative disorder of the elderly, affecting about 1% of those 65 years of age and older and 0.4% of those forty years and older. Mean onset is 57 years, but may begin in childhood and adolescence (juvenile parkinsonism). There are approximately 50,000 new cases diagnosed annually. The pigmented neurons of the substantia nigra, locus caeruleus, and other brain stem dopaminergic cell groups are lost, due to an undefined cause.

Symptomatically, in 50-80% of patients, the disease begins insidiously with a resting 4-8 Hz pill-rolling tremor of one hand. The tremor is maximal at rest, diminishes with movement, and is absent during sleep; it may be significantly enhanced with emotional tension and fatigue. Usually, the hands, arms, and legs are most affected, in that order, but the jaw, tongue, and forehead and eyelids may be affected as well, while the voice remains unaffected.

In many patients, only rigidity occurs without frank tremors. As the rigidity progresses and movements becomes slowed, decreased, and difficult to initiate, muscular aches and sensations of fatigue increase significantly. The face becomes mask like with open mouth and diminished clinking. Posture becomes stooped. Patients have difficulty initiating walking and the gait becomes shuffling with short steps, arms flexed to the waist without any swing with stride. Steps inadvertently quicken and the patient may break into a run to keep from falling (festination). Falls in various directions result from impaired postural reflexes. Speech becomes hypophonic with a monotonous, stuttering dysarthria. Depression is common.

Levo-dopa, the metabolic precursor of dopamine crosses the blood-brain barrier into the basal ganglia where it is decarboxylated to form dopamine, replacing the deficient neurotransmitter. After 2-5 years of treatment with this medication, more than 50% of patients begin to experience fluctuations in their response to levodopa. Amantadine may augment the effects of levodopa and dopamine agonists (bromocriptine and pergolide) directly stimulate dopamine receptors in the basal ganglia. The ominous triad of the disease, side-effects of the anti-parkinsonian drugs, and inactivity result in a significant degree of obstipation, which is unrelenting despite high fiber intake, psyllium, and stool softeners.

Example 4

F.S. is a 45-year old landscape technician, who has had Parkinsonian symptoms since his late 30's. The family history is positive. He has been tried on a variety of Parkinsonian medications, the beneficial actions of which seem to disappear within a few months.

His major complaint was significant muscle weakness and stiffness which was present to the degree that it significantly interfered with his nursery/gardening activities. The hand tremor was present only to a small degree, but the head tremors and tics were very prominent to the degree that he would become nauseated if he kept his vision pinpointed.

He was placed on 5,000 mg of HEPES daily, in divided doses, and his muscular fatigue, stiffness, and tics all disappeared within a three-week period. After another couple of weeks he said he felt like he was before the diagnosis was made and was able to complete all of his lawn/garden service to clients in a timely manner.

Example 5

B.S. is a 83-year old male who has had Parkinsonian symptoms since he was 75 years old. He was placed on levo-dopa with gradual increases to six per day along with large doses of Mirapex and polyethylene glycol for his problem with constipation. His constipation was really quite intractable with abdominal distention and protrusion, nausea and vomiting. Also very worrisome was his diminished deglutitionary activity and tongue biting with oral bleeding. He was unable to stand without assistance and his hesitant walk favored the festinative aspects. Owing to the significance of his disease, he was placed on 6,000 mg of HEPES daily in divided doses, which within three days obviated his swallowing difficulties and abrogated his tongue biting. Over time the daily dosage of levodopa was reduced from the prescribed 6 per day to 2 per day to which a small dose of the dopamine agonist, bromocriptine, was added with singularly beneficial results. His condition improved to the extent that he was again able to drive himself to the store, buy gasoline, and eat out. Most, most gratifying, indeed!

He was placed on an active bowel treatment program with good results which, when required was supplemented with an enema q.o.d. He continued to be monitored closely. His energy level has improved significantly, his facial mask has completely disappeared, and his quality of life vastly improved.

Clinical Cases Based Upon Mechanism of Action of HEPES. Analgesic and Anti-tumor Activities of HEPES-Cancer of the Pancreas Example 6

JWH, a 68-year old white male, who owned and operated a commercial heating and air-conditioning business, had enjoyed good health until September, 2005, when he developed symptoms of fatiguability and intermittent episodes of pain in the upper abdomen with referral through to the back, suggestive of a pancreatic problem. The pain was not relieved by passing bowel movements or any other maneuver. He was seen by his personal physician, who diagnosed Type II diabetes mellitus. He was placed on anti-diabetic medication and diet. No additional studies related to the abdominal pain were carried out, even though they were peculiar in a patient with diabetes. His diabetic state was under satisfactory control with a few weeks, but the abdominal pain problem persisted.

The abdominal pains increased in intensity with new severe pains in the mid-dorsal thoracic spine. In late December, 2005, he suffered an episode of sudden, very intense pain in the spinal area, was seen in the emergency room, where the origin of his spinal pain was found to be secondary to bony metastases. He was hospitalized for work-up and was found to have primary pancreatic cancer with metastases to the liver, lungs, shoulders and thoracic spinal column. He underwent radiation treatments for the thoracic lesions which eased, to a limited extent, the pain in this area.

In consultation with the patient ombudsmen group at M. D. Anderson Hospital in Houston, Tex., the family was told that none of the current study protocols were appropriate for his current condition of cancer of the pancreas with widespread metastases and such advanced disease. He was given 2-4 months to live. It was recommended that he be treated with pain protocols by the local institutions in the Dallas-Fort Worth area. He was treated by his personal physician who placed him on opiate analgesics for pain control.

In February, 2006, his personal physician contacted the present inventors concerning the possible addition of HEPES as he was receiving the maximal level of opiate medication, which was not controlling the pain the patient was experiencing. In March, 2006, he was placed on a daily dosage of the product administered by intravenous infusion, while continuing his maximum opiate analgesic medication. After 5 days of adding the HEPES, his pain was completely controlled. During April, May, and June, 2006, his narcotic medication was slowly reduced owing to the plethora of narcotic-related side-effects (Table 1), with good pain control using about 25% of the maximum dosage of the opiate analgesics.

His quality of life improved significantly at this time. In July, 2006, he developed significant anorexia, probably secondary to the increasing levels of endogenous TNF-alpha (cachectic factor). Dronabinol was recommended, but refused by the patient owing to the medication being derived from marijuana. Thereafter, natural source inhibitors of cachectic factor (Table 2) were recommended, but the patient refused to take any of these as he felt these might interfere with the pain control, which was acceptable. He was then offered parenteral nutritional support, which he declined.

His quality of life was reasonably good, and his condition was such that he was able to take daily 30-minute walks in the mall, was able to attend his 50 year high school reunion in September, 2006, attended in October, 2006, a VIP high school parking lot dedicated to him, went to a dance with his wife in early November, 2006, as well as a high school football game, and celebrated his 69$^{th}$ birthday with the entire family.

From mid-November, 2006, he developed weakness associated with continued weight loss, and from late November became bed-ridden. He continued to suffer from cyctokine-induced (cachectic factor/TNF-alpha) anorexia, which resulted in almost complete inanition, with death ensuing on 19 Dec. 2006. While the death certificate lists the cause of death as cancer of the pancreas, in truth the cause of death was terminal anorexia, inanition, and malnutrition, with more than 65 pound weigh loss.

HEPES administration, however, was associated with improved pain control, reduction in the amount of opiate narcotic analgesia required, elimination of opiate side-effects, a significant anti-tumor effect with several additional months of quality living, which was very much appreciated by the family constellation.

Stabilization of Neural Membranes. Pediatric Autoimmune Neurological Disease Associated with Strep (PANDAS)

Example 7

HSW is an 8-year old boy referred to the present inventors by one of our pediatric neurologists. Historically, at the age of three years, this young boy contracted an infection caused by a very virulent streptococcal micro-organism. It required three courses of antibiotic therapy before the symptoms abated, and apparent recovery took place. About 6-weeks later, he began having involuntary tics involving his head, neck, and shoulders often with flailing arms. Initially, these movements were 10-15 per day. Over the next three months, the athetotic movements increased to 1,300-1,500 per day.

TABLE 1

Side-effects of Opiate Analgesics

Cardiovascular System

Hypotension
Hypertension
Bradycardia
Tachycardia
Palpitations
Pedal Edema
Syncope Central Nervous System Agitation
Sedation
Lightheadedness
Dizziness
Tremors
Seizures
Paresthesias Gastrointestinal System Xerostomia
Anorexia
Nausea
Vomiting
Biliary Tract Spasm
Constipation
Diarrhea
Ileus
Intestinal Obstruction
Elevated Liver Enzyme
Levels Genitourinary System Hesitation in Starting
Urinary Stream
Urinary retention
Antidiuretic Effect
Decreased Libido Integumentary System Facial Flushing
Primary Urticaria
Rashes Musculoskeletal System Muscle Rigidity
Uncoordinated Muscular
Movements
Muscular Weakness Psyche Mood Alteration
Euphoria
Dreams Respiratory System Drug-induced Respiratory
depression leading $CO_2$
retention resulting in
increased CSF pressure &

TABLE 1-continued

Side-effects of Opiate Analgesics increased ICP
Dysphonia
Laryngeal Spasms
Sleep Patterns Insomnia 2° ↑ ICP
Systemic Effects Drug Dependency
Anaphylaxis
Temperature Regulation Diaphoresis
Chills
Visual Disturbances Blurred Vision
Diplopia
Nystagamus
Miosis

TABLE 2

Natural Source Inhibitors of Cachectic Factor (TNF-alpha) (Partial Listing)

| | |
|---|---|
| 1. Aspirin | 13. Colchicine |
| 2. Salicylic Acid | 14. Anandamide |
| 3. Docosahexaenoic Acid (DHA) | 15. Morphine |
| 4. Eicosahenaenoic Acid (EPA) | 16. Resveratrol |
| 5. Quercetin | 17. Myricetin |
| 6. Curcumin | 18. Butylhydroxyacetate (BHA) |
| 7. Epigallocatechin Gallate | 19. PGE$_2$ |
| 8. Capsaicin | 20. Hydroquinone |
| 9. Citrus Flavonoids | 21. Forskolin |
| 10. Narigin | 22. Santamarin |
| 11. Epicatechin | 23. Tetrahydropapaveralione |
| 12. Quinine | 24. 4-Hydroxy-2-noneal |

The pediatric neurologists at numerous medical centers were consulted, with various medications prescribed, which, at best, decreased to a minimal degree the frequency of the movements, but which were accompanied by a number of undesirable side-effects. Over the next 5 years, the parents consulted physicians at various famed medical centers in Scandinavia, Germany, Switzerland, Israel and England, all without any significant improvement. Just prior to his referral to us, he was seen at the NIH, where a very thorough work-up was accomplished, but where the recommendation given the parents was that little could be done or expected as most of the medications available world-wide had been tried without success.

HEPES was cautiously given daily to the youngster in graded intravenous doses owing to the bewildering 1,300-1,500 athetotic movements present. At the end of the first week, having achieved the 70-75 mg/kg level of HEPES administration, the frequency of athetotic movements had been reduced to 10-15 per day. At the end of the second week on the IV product, there was a further reduction in the athetosis with 2-3 movements per day.

The lad was then placed on oral medication at the same daily dosage. During the next three weeks, there were infrequent involuntary athetoid movements triggered by emotional or stressful circumstances. The product was then decreased gradually, with the boy now tic-free without any product being given. It remains moot whether or not there will be a recurrence of the problem, but we are hopeful that the membrane stabilization induced by the HEPES moiety will have a permanent curative effect. This response to HEPES has been considered to be more than miraculous by his parents and other family members, his referring neurologist, as well as the present inventors.

Benzodiazepine Withdrawal Symptoms

Example 8

MS is a 48-year old male, who was initially placed on benzodiazepine medication for panic attacks which presented at age 11. He has been on various forms of medications constituting this group for more than three decades. The dilemma which exists is that often the original condition for which the diazepines are prescribed are considered to be psychiatric in nature. When pain and neurological symptoms appear associated with withdrawal, it is often misdiagnosed with additional medications given which compounds the problem. These medications are recommended for short term treatment (4-6 weeks) only, but as with this patient, usage extends over years. Pain manifestations associated with withdrawal from these drugs are shown in Table 3. One of the major withdrawal symptoms include violent repetitive "tics" which are considerably worsened with emotional situations and other stressors. Abnormal ideation often takes the form of bizarre thoughts as the functioning of the superego is marked impaired. Thus, these patients do things which under normal conditions would never contemplate, much less act out. As a result of these factors, our patient lost his successful business, his houses, and his family comprised of his wife and three beautiful daughters, ages 14, 11, and 7. He walks with a hopping motion associated with bizarre flailing movements of the shoulder and arms. On the internet are listings of more than 300 withdrawal symptoms. The present inventors were consulted on this patient to see if we could ameliorate his extreme pain problems. His neurologic examination was truly strange. One prominent feature was a completely normal ability to dorsiflex his right foot with a 4+ inch elevation, but only a fraction of an inch with his left foot, which also showed tense plantarflexion.

He was started on HEPES by the oral route. After four days on the product, a repeat neurologic examination should normal dorsiflexion of his left foot, equal to that of the right foot, a truly amazing observation. With continued daily product at the 75 mg/kg dosage, he has shown slow improvement manifest by a significant reduction in his athetoid movements, improved gait, more cogent ideation, and significant relief of his pain, which consisted of intense pain in his jaws and teeth, shoulder joints and muscles, precordial chest pain, and sharp pains in the temples bilaterally. He will be closely monitored as to his condition with additional treatment.

In the United States it is estimated that there are between 5-6 million persons with similar histories, and another 2 million in the United Kingdom. If the use of HEPES can ameliorate these dreadful withdrawal symptoms, it will prove to be a significant contribution to easing the distress these patients continually undergo, as the HEPES product enjoys an enviable position of showing no side-effects.

TABLE 3

Pain Syndrome Sites Associated With Benzodiazepine withdrawal

| | |
|---|---|
| 1. | Aching Jaws |
| 2. | Aching Joints |
| 3. | Aching Muscles |
| 4. | Back Pain |
| 5. | Breasts |

TABLE 3-continued

Pain Syndrome Sites Associated With Benzodiazepine withdrawal

| | |
|---|---|
| 6. | Burning Pain of Scalp, Neck, and Shoulders |
| 7. | Ear Aches, frequently recurring |
| 8. | Headaches, often severe |
| 9. | Intense Jaw Pain |
| 10. | Muscular Cramps and Spasms |
| 11. | Neuralgias |
| 12. | Paresthesias of the Scalp |
| 13. | Very Painful Teeth |
| 14. | Chest Pain |
| 15. | Pain with breathing |
| 16. | Sharp Throbbing Pains in Temples |
| 17. | Throbbing Pains in Wrists |
| 18. | Severe Abdominal Cramping Pain |

Reversal of Demyelination Processes

Chronic Inflammatory Demyelinating Polyradiculoneuropathy (CIDP)

CIDP is an autoimmune neuropathy that affects the peripheral motor and sensory nerves. The symptoms are of a slowly progressive numbness and tingling that usually starts in the feet, but later spreads to the legs and hands. The patients also complain of some weakness, again usually starting in the lower extremities, but soon involving the upper extremities as well. With further involvement of the sensory system, other modalities of sensations, such as balance, are affected and the patients complain of inability to walk or maintain balance in the dark. There usually is not bowel or bladder involvement. On rare occasions, cranial nerves are involved and then the symptoms range from difficulty in deglutition to double vision with numbness involving the face. Cognitive skills are not affected by CIDP.

The diagnosis of CIDP is suspected with a history of progressive sensorimotor neuropathy. Physical examination consistent with distal sensory loss in the upper and lower extremities, in conjunction with motor weakness that can be more proximal than distal supports the clinical diagnosis.

Patients may present with pain, numbness or weakness. One of the early signs is a patient who has to use their hands to go upstairs or rise from the squatting position. Some have vasomotor symptoms like difficulty in maintaining their blood pressure, burning sensations which are misdiagnosed as Reflex Sympathetic Dystrophy. Even Complex Regional Pain Syndrome is more likely to be CIDP.

Once the diagnosis is confirmed, treatment with immunosuppressive medications can be initiated. The first line of treatment remains high-dose immunoglobulin which is infused intravenously and tapered over time depending on the patient's improved symptomatology. The use of IV Ig has been shown in numerous studies to improve the symptoms of CIDP.

Example 9

MV is a 43 year old man who presents with a history of multiple allergies, infections (including viral meningitis/aseptic encephalitis), multiple episodes of antibiotic treatments, etc. He describes his physical status historically as follows: "I have been seriously ill since 1991 with progressive neurologic deficits, which culminated with significant loss of motor control in 1993. The condition was misdiagnosed as Multiple Sclerosis with negative findings on Mill." He initially ambulated slowly with the use of a cane. In 1994 he was paralyzed from the neck down. He was treated with Ig intravenously and recovered over a period of weeks. Five months later, he experienced a similar episode. This time the Ig therapy was only weakly helpful, and he as treated with therapeutic plasma exchanges every two weeks.

He has recently been experiencing significant pains in his extremities and HEPES was started orally both for pain control and possible reinforcement of any myelinating defects, as our medical colleagues in the Netherlands have had significant success in reversing the demyelination process. After three weeks on the daily oral product, his pain has been completely controlled, the weakness in his lower extremities has almost completely resolved, and he has expressed his feeling that he feels better than he has for several years.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 5,248,680: Zwitterionic Compounds and Their N-Halo Derivatives for Use in the Treatment of Clinical Conditions.

U.S. Pat. No. 5,716,959: Method of Treating Disease with Piperazine Zwitterion Compounds.

U.S. Patent Application No. 20090149464: Use of 1,4-bis (3-Aminoalkyl) Piperazine Derivatives in the Treatment of Neurodegenerative Diseases.

What is claimed is:

1. A method of treating pain and post-chemotherapy cognitive impairment caused by demyelination in a human subject following a treatment for a cancer comprising the steps of:
   identifying a human subject in need for treatment against the pain post-chemotherapy cognitive impairment caused by demyelination following a treatment for the cancer; and
   administering a pharmaceutical composition comprising N-2-hydroxy-ethyl-piperazine-N'-2-ethane sulfonic acid (HEPES) and derivatives thereof dissolved in sterile water, buffer, saline or other pharmaceutically acceptable carriers once daily at a dosage of 10-100 mg/kg of body weight, wherein the pharmaceutical composition is administered orally, subcutaneously, parenterally, intravenously, peritoneally, or intramuscularly that is sufficient to treat the pain and post-chemotherapy cognitive impairment caused by demyelination.

2. The method of claim 1, wherein the cancer is a pancreatic cancer, breast cancer, colorectal cancer, ovarian cancer, lung cancer, cervical cancer, gastric cancer, liver cancer, melanomas, brain tumors, multiple myeloma, prostate cancer, or bladder cancer.

3. The method of claim 1, wherein the composition is used to treat post-chemotherapy cognitive impairment following a breast cancer treatment.

4. The method of claim 1, wherein the HEPES is dissolved in sterile water for injection.

* * * * *